United States Patent
Chung

(10) Patent No.: US 8,883,148 B2
(45) Date of Patent: Nov. 11, 2014

(54) PREVENTION OF JOINT DESTRUCTION

(75) Inventor: Yih-Lin Chung, Taipei (TW)

(73) Assignee: ASAN Laboratories Company (Cayman), Limited, Shenkeng Shiang, Taipei County (TW)

( * ) Notice: Subject to any disclaimer, the term of this patent is extended or adjusted under 35 U.S.C. 154(b) by 1817 days.

(21) Appl. No.: 11/079,370

(22) Filed: Mar. 14, 2005

(65) Prior Publication Data

US 2005/0245439 A1      Nov. 3, 2005

Related U.S. Application Data

(63) Continuation-in-part of application No. 10/132,999, filed on Apr. 26, 2002, now abandoned.

(51) Int. Cl.

| | | |
|---|---|---|
| A61K 39/395 | (2006.01) | |
| A61K 9/127 | (2006.01) | |
| A61K 31/165 | (2006.01) | |
| A61K 47/10 | (2006.01) | |
| A61K 31/19 | (2006.01) | |
| A61K 9/00 | (2006.01) | |
| A61K 47/06 | (2006.01) | |
| A61K 38/15 | (2006.01) | |
| A61K 47/38 | (2006.01) | |
| A61K 31/445 | (2006.01) | |

(52) U.S. Cl.
CPC ............... *A61K 9/127* (2013.01); *A61K 31/165* (2013.01); *A61K 47/10* (2013.01); *A61K 31/19* (2013.01); *A61K 9/0014* (2013.01); *A61K 47/06* (2013.01); *A61K 38/15* (2013.01); *A61K 47/38* (2013.01); *A61K 31/445* (2013.01); *A61K 9/0019* (2013.01)

USPC ........ 424/131.1; 514/282; 514/561; 514/557; 514/570; 514/569

(58) Field of Classification Search
USPC ........ 424/131.1; 514/282, 561, 557, 570, 569
See application file for complete search history.

(56) References Cited

U.S. PATENT DOCUMENTS

| | | | | |
|---|---|---|---|---|
| 5,281,623 A | | 1/1994 | Clemens et al. ............... | 514/654 |
| 5,418,252 A | * | 5/1995 | Williams ...................... | 514/443 |
| 5,605,930 A | * | 2/1997 | Samid .......................... | 514/510 |
| 5,852,056 A | * | 12/1998 | Samid .......................... | 514/510 |
| 5,993,845 A | | 11/1999 | Geerts et al. .................. | 424/423 |
| 6,028,109 A | * | 2/2000 | Willson ....................... | 514/567 |

(Continued)

FOREIGN PATENT DOCUMENTS

| | | |
|---|---|---|
| WO | WO9937150 A1 * | 7/1990 |
| WO | WO 98/29109 A1 | 9/1998 ............. A61K 31/00 |

(Continued)

OTHER PUBLICATIONS www.merriam-webster.com/dictionary/prevent, Nov. 13, 2007.*

(Continued)

*Primary Examiner* — Benjamin Packard
(74) *Attorney, Agent, or Firm* — Cesari and McKenna, LLP

(57) ABSTRACT

A method for treating, preventing or reducing the risk of joint destruction in a subject who suffers from a joint or musculoskeletal disease. The method comprises administering a histone deacetylase (HDAC) inhibitor or in conjunction with other agents to inhibit degradation and resorption of cartilage and bone in the joint.

15 Claims, 8 Drawing Sheets
(4 of 8 Drawing Sheet(s) Filed in Color)

(56) References Cited

U.S. PATENT DOCUMENTS

| | | | |
|---|---|---|---|
| 6,077,823 A * | 6/2000 | Kuberasampath et al. | 514/12 |
| 6,124,495 A | 9/2000 | Neiss et al. | 560/104 |
| 6,225,294 B1 * | 5/2001 | Daifotis et al. | 514/108 |
| 6,313,091 B1 * | 11/2001 | Wisniewski et al. | 514/12 |
| 6,403,555 B1 | 6/2002 | Skov | 514/10 |
| 6,548,479 B1 | 4/2003 | Skov | 514/10 |
| 2003/0082666 A1 * | 5/2003 | Kammer et al. | 435/18 |
| 2003/0114525 A1 | 6/2003 | Kammer et al. | 514/557 |
| 2003/0134865 A1 | 7/2003 | Adcock et al. | 514/263.34 |

FOREIGN PATENT DOCUMENTS

| | | | | |
|---|---|---|---|---|
| WO | WO 9926657 A1 * | 6/1999 | | |
| WO | WO0008048 A1 * | 2/2000 | | |
| WO | WO 01/17514 A1 | 3/2001 | | A61K 31/00 |
| WO | WO 02/26703 | * 4/2002 | | C07C 323/60 |

OTHER PUBLICATIONS

Goldring et al, Mechanisms of bone loss in inflammatory arthritis: diagnosis and therapeutic implications, Arthritis Res 2000, 2:33-37.*

Kitamura et al (British Journal of Haematology, 108 (2000) 696-702).*

Mishra et al., "Histone Deacetylase Inhibitor Trichostatin A as a Strong Candidate for Treatment of Systemic Lupus Erythematosus", FASEB Journal, 5:A1214, Mar. 2001.

Mishra et al., "Trichostatin A Reversees Skewed Expression of CD154, Interleukin-10, and Interferon-Gamma Gene and Protein Expression in Lupus T Cells", Proceedings of the National Academy of Sciences of USA 98(5):2628-2633, 2001.

Richon et al., "Histone Deacetylase Inhibitor Selectively Induces P21 WAF1 Expression and Gene-Associated Histone Acetylation", PNAS, 97(18):10014-10019, Aug. 28, 2009.

Witt et al., "Induction of Fetal Hemoglobin Expression by the Histone Deacetylase Inhibitor Apicidin", Blood 101(5), Mar. 1, 2003.

* cited by examiner

Blank control

HDAC inhibitor-treated

PREVENTION OF JOINT DESTRUCTION

This application is a continuation-in-part of U.S. application Ser. No. 10/132,999, filed Apr. 26, 2002, the entire disclosure of which being incorporated by reference herein in its entirety.

BACKGROUND

The present invention relates to the use of a histone deacetylase (HDAC) inhibitor or in conjunction with other agents to treat, prevent or reduce the risk of joint destruction in a subject who suffers from a joint or musculoskeletal disease by inhibiting degradation and resorption of cartilage and bone in the joint.

The development of joint destruction is usually associated with spondyloarthropathy, rheumatoid arthritis, degenerative joint disease, gout, infection, cancer, or trauma.

The spondyloarthropathy family consists of undifferentiated spondyloarthropathy, ankylosing spondylitis, juvenile onset ankylosing spondylitis, reactive arthritis, Reiter's syndrome, psoriatic arthritis, and spondyloarthropathy associated with Crohn's disease and ulcerative colitis. Distinctive features of spondyloarthropathy include asymmetric arthritis, enthesitis, genital and skin lesions, eye and bowel inflammation, and association with preceding or ongoing infectious disorders, and a strong association with human leukocyte antigen (HLA) B27. The peripheral arthritis in spondyloarthropathy is of acute onset and predominantly involves the lower extremities, especially the knees, ankles, and feet. It is typically asymmetrical and often affects only one to three joints. Sausage digits (dactylitis), sacroilitis, and spine enthesopathy are diagnostic of spondyloarthropathy. The real cause of spondyloarthropathy remains unknown. The other destructive arthropathy that needs to be distinguished from spondyloarthropathy is rheumatoid arthritis that is an autoimmune disease. Symmetrical polyarthritis of the small joints is characteristic of rheumatoid arthritis. Although the etiology of spondyloarthropathy is different from that of rheumatoid arthritis, the major pathology of the affected joints consists of in common inflammation of the synovial and extrasynovial structures such as the tendons and ligaments, inflammatory cell infiltration around joint soft tissues, production of proinflammatory mediators and enzymes from macrophages, monocytes and fibroblasts, synovial cell proliferation, and degradation and resorption of cartilage and bone, which all contribute to the destruction of the joint structure. Joint destruction occurs at the site of insertion of joint capsule, ligaments or tendons. Since the area is highly vascular, it is susceptible to bacterial invasion and antigen deposition.

To date, the current available therapies all aim at suppressing the acute exacerbation of joint inflammation and pain, but only to suppress the inflammatory or immune reaction is still not enough to stop the chronic process of the cartilage and bone degradation and resorption that results in joint destruction (Lee, D M., et al., Lancet 358: 903-911, 2001). The natural course of spondyloarthropathy and rheumatoid arthritis is one of periods of exacerbation and remission for life, and fatalities are usually due to the iatrogenic effects of therapy, such as gastrointestinal bleeding related to long-term use of nonsteroidal anti-inflammatory drugs (NSAIDs) and infection or hepatorenal toxicity associated with chronic use of steroids, immunosuppressive agents, and other disease-modifying antirheumatoid drugs (DMARDs). Although clinical trials that neutralize the major pro-inflammatory cytokine, tumor necrosis factor-$\alpha$ (TNF-$\alpha$), by injection of either antibodies against TNF-$\alpha$ or soluble TNF-$\alpha$ receptors have produced some therapeutic anti-inflammatory effects, the major concerns are that the treatment must be administrated continually, the duration of efficacy appears to decrease with repeated doses, cessation may be associated with an increase in disease activity, the long-term usage increases the opportunity of infection, and the process of joint destruction is not stopped (Moreland, L W., et al., N. Engl. J. Med. 337: 41-147, 1997). Thus, there is an urgent need for effective therapies for preventing joint destruction and maintaining functional status.

SUMMARY

According to the present invention, it was surprisingly found that administration of a histone deacetylase (HDAC) inhibitor is effective in preventing the joint destruction by inhibiting degradation and resorption of cartilage and bone.

A method for treating, preventing, or reducing the risk of joint destruction in a subject who suffers from a joint or musculoskeletal disease is provided. The method comprises administering to the subject a therapeutically effective amount of a HDAC inhibitor or a pharmaceutically acceptable salt thereof, or in conjunction with other agents, and a pharmaceutically acceptable carrier to inhibit degradation and resorption of cartilage and bone in the joint.

The compounds of the present invention can be administered orally, intraarticularly, intraperitoneally, intrathecally, intrarterially, intranasally, intraparenchymally, subcutaneously, intramuscularly, intravenously, dermally, intrarectally, and topically. The dosage amounts are based on the effective concentration observed in vitro and in vivo studies. The varied and efficacious utility of the compounds of the present invention is further illustrated by the finds that they may also be administered concomitantly, sequentially or in combination with an agent such as a second HDAC inhibitor, an organic bisphosphonate, a chemotherapeutic agent, a radiopharmaceutical agent, a TNF-alpha antagonist, a non-steroid anti-inflammation drug, a steroid, an anti-oxidant agent, an angiogenesis inhibitor, a matrix metalloproteinase inhibitor, a vitamin, a selective estrogen receptor modulator (SERM), estrogen-progestin, an androgen, calcitonin, an antibiotics, a cathepsin K inhibitor, an inhibitor of osteoclast proton ATPase, an inhibitor of HMG-CoA reductase, a statin, an integrin receptor antagonist, an osteoblast anabolic agent, and a selective serotonin reuptake inhibitor, or a pharmaceutically acceptable salt or mixture thereof.

BRIEF DESCRIPTION OF THE DRAWINGS

The file of this patent contains at least one drawing executed in color. Copies of this patent with color drawings will be provided by the Patent and Trademark Office upon request and payment of the necessary fee.

The present invention will be more fully understood and further advantages will become apparent when reference is made to the following description of the invention and the accompanying drawings in which:

FIG. 1A shows the net swelling of paw volume of blank control, cream vehicle, and phenylbutyrate cream treatment at different days; FIG. 1B shows that of ointment control and trichostatin A ointment treatment at different days.

FIG. 3A shows H & E staining; FIG. 3B shows p16$^{INK4}$ immunohistochemistry result. FIGS. 3A and 3B are at 200× field.

FIG. 4A is control group; FIG. 4B HDAC inhibitor-treated group. The black arrow indicates the destructed ankle joint in the control group.

FIG. 5A is control group; FIG. 5B HDAC inhibitor-treated group. The black arrow indicates the degradation and resorption in the cartilage and bone of the joint by the proliferating synovium invasion in the control group. FIGS. 5A and 5B are at 40× field.

FIG. 6A is control group; FIG. 6B HDAC inhibitor-treated group. The black arrow indicates the site of infiltration of inflammatory cells and bone degradation in a destructive joint in the control group. FIGS. 6A and 6B are at 100× field.

DETAILED DESCRIPTION

Figure 1A:
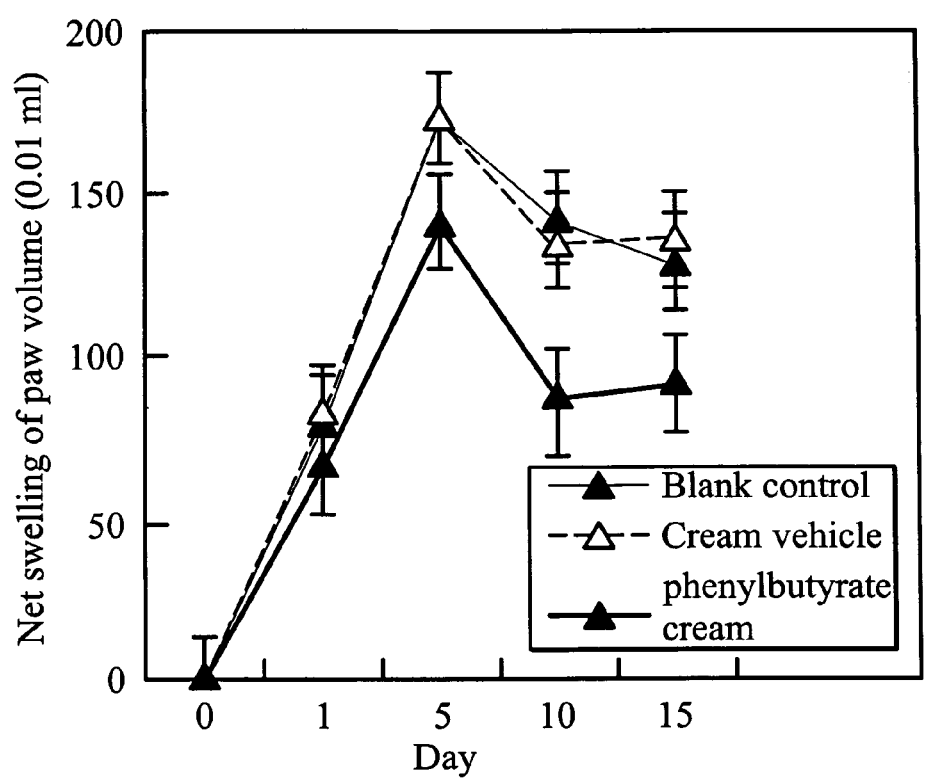
FIGS. 1A and 1B are diagrams showing the effect in suppression of joint swelling in an animal model of a destructive joint disease by the HDAC inhibitors.

The invention is preferably used to treat, prevent or reduce the risk of joint destruction in a subject who suffers from rheumatoid arthritis, spondyloarthropathies (especially undifferentiated spondyloarthropathy, ankylosing spondylitis, juvenile onset ankylosing spondylitis, reactive arthritides, Reiter's syndrome, psoriatic arthropathy, and spondyloarthropathy associated with Crohn's disease and ulcerative colitis), or other destructive joint or musculoskeletal diseases such as bone loss, bone fractures, osteonecrosis, osteoporosis, osteopenia, glucocorticoid induced osteoporosis, Paget's disease, abnormally increased bone turnover, periodontal disease, tooth loss, periprosthetic osteolysis, degenerative joint disease, gouty arthritis, septic arthritis, osteogenesis imperfecta, bone cancer, multiple myeloma, hypercalcemia of malignancy, metastatic bone disease, and paraneoplastic syndrome. The osteoporosis or osteopenia is secondary to immobilization, osteodystrophy, cachexia, anorexia nervosa, exercise induced amenorrhea, chemotherapy or radiotherapy-induced amenorrhea, androgen deprivation therapy, Turner syndrome, cystic fibrosis, diabetes mellitus, hyperthyroidism, hyperparathyroidism, Cushing's syndrome, glucocorticoid excess, acute lymphoblastic leukemia, Klinefelter's and Kallman's syndromes, alcohol abuse, cigarette smoking, connective tissue disease, or osteoarthritis.

Joint destruction results from degradation and resorption in cartilage and bone of the joint. Bone resorption and apposition is a balance controlled by two distinct cell types, osteoclasts and osteoblasts, respectively. These cells are in closed relation by cell contacts, cytokines, growth factors and hormones. Interleukine (IL)-6 and Receptor of Activator of NF-κB Ligand (RANK-L) have been identified as the major cytokines implicated in osteoblast/osteoclast communications. RANK-L is expressed on stromal cells/osteoblasts and its interaction with the receptor RANK, present on osteoclast precursors and mature osteoclasts induces their differentiation and/or activation (Chambers, T J., et al., J. Pathol. 192: 4-13, 2000). Disturbance of the IL-6/RANK-L/RANK/NF-κB functional balance is responsible for osteolysis (degradation) and resorption within the bone. For example, the pathogenesis of joint destruction can be initiated by overproduction of IL-6 by osteoblasts, macrophages, lymphocytes, fibroblast, or cancer cells from inflammation, immune reaction, infection, or neoplasia, which activates osteoclasts to increase bone resorption, and then release matrix-associated cytokines such as IL-1β and TNF-α and growth factor such as TGF-β and enzymes such as matrix metaloproteinases (MMPs) for cartilage and bone degradation. On the other hand, these cytokines and growth factors also increase the IL-6 production via a positive feedback loop. Then a vicious cycle takes place to amplify the signal for degradation and resorption of cartilage and bone, leading to joint destruction. However, in clinical trials, either blocking the cytokine activity by TNF-α antagonists and the enzyme activity by MMP inhibitors or suppressing the inflammatory reactions by NSAIDs or steroids and the immune reaction by DMARDs has failed to stop the process of joint destruction despite of amelioration of joint inflammation. One of the possible reasons is that the mesenchymal and fibroblast-like synovial cells can be transformed in response to the inflammatory cytokine milieu, and become a locally invasive malignancy-like that, if unchecked, can directly degrade cartilage and bone of the joint as well as indirectly resorb the cartilage and bone via the IL-6/RANK-L/RANK/NF-κB pathway (Muller-Ladner, U., et al., Am. J. Pathol. 149:1607-1615, 1996).

The drugs, which have in the past been used to treat destructive joint diseases, such as spondyloarthropathy and rheumatoid arthritis, are based on symptomatic anti-inflammatory treatments or disease modifying treatments. The dominating drugs for symptomatic treatments are NSAIDs, systemic steroids, or intraarticular injections of glucocorticosteroids. The DMARDs include drugs which, by influencing the immune reactions of the body, reduce joint inflammation. Examples of DMARDs include methotrexate, azathioprine, gold salts, cyclophosphamide and sulphasalazine. All of these treatments unfortunately cause severe side effects and are not particularly effective. For example, glucocorticoid administration is generally directed against the local inflammation, i.e. it has been used to treat directly the inflammatory cells present in the joint inflammation. The administration of high dose steroid or DMARDs results in severe side effects on the body, including effects on the skeleton and muscles, and infection. Although TNF-α antagonists may show an anti-inflammation effect in some patients with spondyloarthropathy and rheumatoid arthritis, they still cannot prevent the process of joint destruction. Moreover, development of active tuberculosis and demyelinating central nervous system disease has been recognized as serious adverse effects of anti-TNF-α therapies (Baeten, D., et al., Ann. Rheum. Dis. 62:829, 2003).

The use of an HDAC inhibitor or in conjunction with other agents to prevent joint destruction in a joint or musculoskeletal disease has not theretofore been suggested or disclosed. The present invention reveals that the use of the HDAC inhibitor or in conjunction with other agents can treat, prevent, or reduce the risk of joint destruction by inhibiting degradation and resorption of cartilage and bone in the joint.

HDAC inhibitors as a class of compounds with abilities in multiple gene regulation can modulate the expression of a specific set of genes by increasing histone acetylation, thereby regulating chromatin structure and accessibility of target genes for transcription and thus treating diseases (Marks, P A., et al., J. Natl. Cancer Inst., 92: 1210-6, 2000).

HDAC inhibitors act selectively on gene expression, altering the expression of only about 2% of the genes expressed in cultured tumor cells. Histone hyperacetylation results in the up-regulation of cell-cycle inhibitors (p21Cip1, p27Kip1, and p16INK4), the down-regulation of oncogenes (Myc and Bcl-2), the repression of inflammatory cytokines (IL-1β, IL-8, TNF-α, and TGF-β), or no change (GAPDH and γ-actin)(Lagger et al, EMBO J., 21: 2672-81, 2002; Richon et al, Clin. Cancer Res., 8: 662-667, 2002; Richon et al, Proc. Natl. Acad. Sci. USA., 97: 10014-9, 2000; Van Lint et al, Gene Expr., 5: 245-3, 1996; Huang et al, Cytokine, 9: 27-36, 1997; Mishra et al, Proc. Natl. Acad. Sci. USA., 98: 2628-33, 2001; Stockhammer et al, J. Neurosurg., 83: 672-81, 1995; Segain et al, Gut, 47: 397-403, 2000; Leoni et al, Proc. Natl. Acad. Sci. USA, 99: 2995-3000, 2002). In addition to inducing histone hyperacetylation, HDAC inhibitors also induce hyperacetylation of nonhistone proteins such as ribosomal S3, p53 or the Rel-A subunit of NF-κB, modulate protein kinase C (PKC) activity, inhibit protein isoprenylation, decrease DNA methylation, and bind to nuclear receptors (Webb et al, J. Biol. Chem., 274: 14280-7, 1999; Chen et al, Science, 293: 1653-7, 2001). More and more different mechanisms also pointed to inhibition of NF-κB transcriptional activity after treatment with HDAC inhibitors. HDAC inhibitors have exhibited properties in inducing cell-cycle arrest, cell differentiation, and apoptotic cell death in tumor cells and in decreasing inflammation reaction in inflammatory diseases (Warrell et al, J. Natl. Cancer Inst., 90: 1621-5, 1998; Vigushin et al, Clin. Cancer Res., 7: 971-6, 2001; Saunders et al, Cancer Res., 59: 399-404, 1999; Gottlicher et al, EMBO J., 20: 6969-78, 2001; Rombouts et al, Acta Gastroenterol. Belg., 64: 239-46, 2001). The abilities in modification of chromatin structure and NF-κB activity suggest that HDAC inhibitors could be therapeutic candidates not only for cancers but also for inflammatory diseases.

Thus, based on the actions of the HDAC inhibitors, the use of HDAC inhibitors is expected to suppress the major proinflammatory cytokine (TNF-α and IL-6) production, the NF-κB activity and the inflammatory cell infiltration, and demonstrate an anti-inflammatory effect in the joint disease. Although so far agents such as NSAID, steroid, DMARD and TNF-α antagonist all aimed at anti-inflammation or immunosuppression have not shown effects in preventing joint destruction, in the present invention it has surprisingly been found that in addition to suppressing inflammation the use of HDAC inhibitors can effectively prevent the joint destruction by inhibiting the degradation and resorption of bone and cartilage of the joint.

Active compounds used to carry out the present invention are, in general, histone hyperacetylating agents, such as HDAC inhibitors. Numerous such compounds are known. See, e.g., P. Dulski, Histone Deacetylase as Target for Antiprotozoal Agents, PCT Application WO 97/11366 (Mar. 27, 1997). Examples of such compounds include, but are not limited to:

A. Trichostatin A and its analogues such as: Trichostatin A (TSA); and Trichostatin C (Koghe et al. 1998. Biochem. Pharmacol. 56:1359-1364) (Trichostatin B has been isolated but not shown to be an HDAC inhibitor).

B. Peptides, such as: Oxamflatin [(2E)-5-[3-[(phenylsufonyl) aminophenyl]-pent-2-en-4-ynohydroxamic acid (Kim et al. Oncogene, 18:2461-2470 (1999)); Trapoxin A (TPX)-cyclic tetrapeptide (cyclo-(L-phenylalanyl-L-phenylalanyl-D-pipecolinyl-L-2-amino-8-oxo-9,10-epoxy-decanoyl)) (Kijima et al., J. Biol. Chem. 268, 22429-22435 (1993)); FR901228, depsipeptide (Nakajima et al., Ex. Cell Res. 241, 126-133 (1998)); FR225497, cyclic tetrapeptide (H. Mori et al., PCT Application WO 00/08048 (Feb. 17, 2000)); Apicidin, cyclic tetrapeptide [cyclo(N-O-methyl-L-tryptophanyl-L-isoleucinyl-D-pipecolinyl-L-2-amino-8-oxodecanoyl)] (Darkin-Rattray et al., Proc. Natl. Acad. Sci. USA 93, 13143-13147 (1996)); Apicidin Ia, Apicidin Ib, Apicidin Ic, Apicidin IIa, and Apicidin IIb (P. Dulski et al., PCT Application WO 97/11366); HC-Toxin, cyclic tetrapeptide (Bosch et al., Plant Cell 7, 1941-1950 (1995)); WF27082, cyclic tetrapeptide (PCT Application WO 98/48825); and chlamydocin (Bosch et al., supra).

C. Hydroxamic acid-based hybrid polar compounds (HPCs), such as: salicylihydroxamic acid (SBHA) (Andrews et al., International J. Parasitology 30, 761-8 (2000)); suberoylanilide hydroxamic acid (SAHA) (Richon et al., Proc. Natl. Acad. Sci. USA 95, 3003-7 (1998)); azelaic bishydroxamic acid (ABHA) (Andrews et al., supra); azelaic-1-hydroxamate-9-anilide (AAHA) (Qiu et al., Mol. Biol Cell 11, 2069-83 (2000)); M-carboxycinnamic acid bishydroxamide (CBHA) (Ricon et al., supra); 6-(3-chlorophenylureido)carpoic hydroxamic acid (3-Cl-UCHA) (Richon et al., supra); MW2796 (Andrews et al., supra); and MW2996 (Andrews et al., supra). Note that analogs not effective as HDAC Inhibitors are: hexamethylene bisacetamide (HBMA) (Richon et al. 1998, PNAS, 95:3003-7); diethyl bix(pentamethylene-N,N-dimethylcarboxami-de)malonate (EMBA) (Richon et al. 1998, PNAS, 95:3003-7); pyroxamide, scriptaid, PXD-101, and LAQ-824.

D. Short chain fatty acid (SCFA) compounds, such as: sodium butyrate (Cousens et al., J. Biol. Chem. 254, 1716-23 (1979)); isovalerate (McBain et al., Biochem. Pharm. 53:1357-68 (1997)); valproic acid; valerate (McBain et al., supra); 4-phenylbutyrate (4-PBA) (Lea and Tulsyan, Anticancer Research, 15, 879-3 (1995)); phenylbutyrate (PB) (Wang et al., Cancer Research, 59, 2766-99 (1999)); propionate (McBain et al., supra); butrymide (Lea and Tulsyan, supra); isobutyramide (Lea and Tulsyan, supra); phenylacetate (Lea and Tulsyan, supra); 3-bromopropionate (Lea and Tulsyan, supra); and tributyrin (Guan et al., Cancer Research, 60, 749-55 (2000)); arginine butyrate, isobutyramide, and valproate.

E. Benzamide derivatives, such as: MS-27-275 [N-(2-aminophenyl)-4-[N-(pyridin-3-yl-methoxycarbonyl) aminomethyl] benzamide] (Saito et al., Proc. Natl. Acad. Sci. USA 96, 4592-7 (1999)); and 3'-amino derivative of MS-27-275 (Saito et al., supra); and CI-994.

F. Other inhibitors, such as: depudecin [its analogues (mono-MTM-depudecin and depudecin-bisether) do not inhibit HDAC] (Kwon et al. 1998. PNAS 95:3356-61); and scriptaid (Su et al. 2000 Cancer Research, 60:3137-42).

Histone deacetylases (HDACs) as that term is used herein are enzymes which catalyze the removal of acetyl groups from lysine residues in the amino terminal tails of the nucleosomal core histones. As such, HDACs together with histone acetyl transferases (HATs) regulate the acetylation status of histones. Histone acetylation affects gene expression and inhibitors of HDACs, such as the hydroxamic acid-based hybrid polar compound suberoylanilide hydroxamic acid (SAHA) induce growth arrest, differentiation and/or apoptosis of transformed cells in vitro and inhibit tumor growth in vivo. HDACs can be divided into three classes based on structural homology. Class I HDACs (HDACs 1, 2, 3 and 8) bear similarity to the yeast RPD3 protein, are located in the nucleus and are found in complexes associated with transcriptional co-repressors. Class II HDACs (HDACs 4, 5, 6, 7 and 9) are similar to the yeast HDA1 protein, and have both nuclear and cytoplasmic subcellular localization. Hydroxamic acid-based HDAC inhibitors, such as SAHA, inhibit both Class I and II HDACs. Class III HDACs form a structurally distant class of nicotinamide (NAD) dependent enzymes that are related to the yeast SIR2 proteins and are not inhibited by hydroxamic acid-based HDAC inhibitors.

HDAC inhibitors, as that term is used herein are compounds which are capable of inhibiting the deacetylation of histones in vivo, in vitro or both. As such, HDAC inhibitors inhibit the activity of at least one histone deacetylase. As a result of inhibiting the deacetylation of at least one histone, an increase in acetylated histones occurs and accumulation of acetylated histones is a suitable biological marker for assessing the activity of HDAC inhibitors. Therefore, procedures which can assay for the accumulation of acetylated histones can be used to determine the HDAC inhibitory activity of compounds of interest. It is understood that compounds which can inhibit histone deacetylase activity can also bind to other substrates and as such can inhibit other biologically active molecules such as enzymes or non-histone proteins.

The HDAC inhibitor agents can be brought in the form of pharmaceutically acceptable salts. As such pharmaceutically acceptable salts may be used so long as they do not adversely affect the desired pharmacological effects of the compounds. The selection and production can be performed by those skilled in the art. Examples of pharmaceutically acceptable salts include alkali metal salts such as a sodium salt or a potassium salt, alkaline earth metal salts such as a calcium salt or a magnesium salt, salts with an organic base such as an ammonium salt, or a salt with an organic base such as a triethylamine salt or an ethanolamine salt.

The HDAC inhibitor agents of the present invention may be administered orally or non-orally. In the case of oral administration, they may be administered in the form of soft and hard capsules, tablets, granules, powders, solutions, suspensions, mouthwash or the like. In the case of non-oral administration, they may be administered in the form of creams, ointments, gels, lotions, patches, suppositories, liposome formations, injection solution, drip infusion formulations, enema or the like whereby continued membrane absorption can be maintained in the form of solid, viscous liquid, broadhesive substance or suspension. The selection of the method for the preparation of these formulations and the vehicles or carriers, disintegrators or suspending agents, can be readily made by those skilled in the art. The bisphosphonates and HDAC inhibitors of the present invention may contain a further composition or other agents and a pharmaceutically acceptable carrier or a pharmaceutically acceptable salt thereof.

Another embodiment of the invention is to combine the HDAC inhibitors with an organic bisphosphonate for treating, preventing or reducing the risk of joint destruction. Bisphosphonates are potent inhibitors of bone resorption used for the treatment and prevention of osteoporosis. In general, bisphosphonates have in common the P—C—P structure, which is similar to the P—O—P structure of native pyrophosphate. Bisphosphonates differ from each other only at the two "R" groups. Examples of such compounds include, but are not limited to: alendronate, cimadronate, clodronate, tiludronate, etidronate, ibandronate, neridronate, olpandronate, risedronate, piridronate, pamidronate, and zolendronate (Rodan, G A., et al., J. Clin. Nvest. 97:2692, 1996). The bisphophonates inhibit osteoclastic bone resorption via a mechanism that differs from that of other antiresorptive agents such as estrogen. Bisphophonates attach to body surfaces, especially surface undergoing active resorption. When osteoclasts begin to resorb bone that is impregnated with bisphosphonate, the bisphophonate released during resorption impairs the ability of the osteoclasts to form the ruffled border, to adhere to the bony surface, and to produce the protons necessary for continued bone resorption (Colucci, S., et al., Calcif. Tissue Int. 63:230, 1998). In addition to the resorption-mediated release of bisphophonate from bone surfaces, the mechanisms of bisphophonates to impair the osteoclast activation also include inhibition of IL-6 production, stimulation of formation of osteoblast precursors, inhibition of proliferation of osteoclast precursors, induction of apoptosis in osteoclasts, and inhibition of osteoclast cholesterol synthesis via inhibition of the enzyme farnesyldiphosphate synthase (Reszka, A A., et al., J. Biol. Chem. 274:34967, 1999; Tokuda, H., et al., J. Cell Biochem. 69:252, 1998). Thus, the combined use of the HDAC inhibitors and bisphosphonates relates to another embodiment of the invention for prevention of joint destruction in more destructive diseases such as rheumatoid arthritis, degeneration, trauma, and cancer.

As recognized by those skilled in the art, the effective doses vary depending on route of administration, excipient usage, and the possibility of co-use with another therapeutic treatment such as the use of a second HDAC inhibitor, an organic bisphosphonate, a chemotherapeutic agent, a radiopharmaceutical agent, a TNF-alpha antagonist, a non-steroid anti-inflammation drug, a steroid, an anti-oxidant agent, an angiogenesis inhibitor, a matrix metalloproteinase inhibitor, a vitamin, a selective estrogen receptor modulator (SERM), estrogen-progestin, an androgen, calcitonin, an antibiotics, a cathepsin K inhibitor, an inhibitor of osteoclast proton ATPase, an inhibitor of HMG-COA reductase, a statin, an integrin receptor antagonist, an osteoblast anabolic agent, or a selective serotonin reuptake inhibitor or a pharmaceutically acceptable salt or mixture thereof. Effective amounts and treatment regimens for any particular subject (e.g., human, dog, or cat) will also depend upon a variety of other factors, including the activity of the specific compound employed, age, body weight, general health status, sex, diet, time of administration, rate of excretion, severity and course of the disease, and the patient's disposition to the disease, but are usually from 0.001% to 100% by weight of the composition irrespective of the manner of administration. Active compounds of the present invention may optionally be administered in conjunction with other compounds useful in treating, preventing or reducing the risk of joint destruction in a subject who suffers from a joint or musculoskeletal disease such as spondyloarthropathy, rheumatoid arthritis, and other destructive joint diseases resulting from trauma, degeneration, or cancer. The other compounds may optionally be administered concurrently or sequentially. As used herein, the word "concurrently" means sufficiently close in time to produce a combined effect (that is, concurrently may be simultaneously, or it may be two or more events occurring within a short time period before or after each other). As used herein, the administration of two or more compounds "concurrently" or "in combination" means that the two compounds are administered closely enough in time that the presence of one alters the biological effects of the other. The two or more compounds may be administered simultaneously or sequentially. Simultaneous administration may be carried out by mixing the compounds prior to administration, or by administering the compounds at the same point in time but at different anatomic sites or using different routes of administration.

In order that the invention described herein may be more readily understood, the following examples are set forth. It should be understood that the examples are for illustrative purpose only and are not to be construed as limiting this invention in any manner. All references cited herein are expressly incorporated by reference in their entirety.

EXAMPLE

Example 1

Prevention of Joint Destruction

The animal model for a destructive joint disease has been established and characterized well (Winter C A, et al., Arthritis Rheum. 9:394-404, 1966). Long Evans rats weighing 150±20 g and ICR derived male mice weighing 22±2 g were used. Space allocation for 5 mice was 45×23×15 cm. The animals were housed in APEC® (Allentown Gaging, Allentown, N.J., USA) cages and maintained in a hygienic environment under controlled temperature (22-24° C.) and humidity (60-80%) with 12-hours light/dark cycles for at least one week. A well-ground suspension of killed Mycobacterium tuberculosis (DIFCO, USA; 0.3 mg in 0.1 ml of light mineral oil; Complete Freund's Adjuvant, CFA) was administered into the subplantar region of the right hind paw immediately after first dosing of the HDAC inhibitor on first day (denoted day 1). The topical formulations containing HDAC inhibitors had been made by us before (Chung, Y L., et al., Mol. Cancer Ther. 3:317-325, 2004). The 1% of phenylbutyrate sodium cream (an HDAC inhibitor) at a dose of 200 mg/paw or the 0.1% of trichostatin A (an HDAC inhibitor) ointment at a dose of 10 mg/paw were applied topically to the whole right hind paw surface twice daily for 18 consecutive days. Hind paw volume was measured by Plethsmometer (Cat. No. 7150, UGO BASILE, Italy) and Water cell (25 mm diameter, Cat. No. 7157, UGO BASILE, Italy) on day 0 (before CFA treated), 1, 5, 10, and 15 after CFA of right paw (with CFA). At Day 18, the right hind paws were taken from blank and vehicles control groups, and the treatment groups. Each group had 6 animals. Some fresh tissues were subjected to northern blot analysis for the level of TNF-α expression in the joint. Tissues were also fixed in 10% phosphate-buffered formalin (pH 7.4), decalcified in 10% EDTA, and embedded in paraffin. Sections (3 μm thick) were stained with hematoxylin and eosin (H&E) and immunostained with antibodies of p16INK4 to examine the joint structure.

The results show that:

a. The HDAC inhibitor suppresses the joint swelling.

Figure 1B:
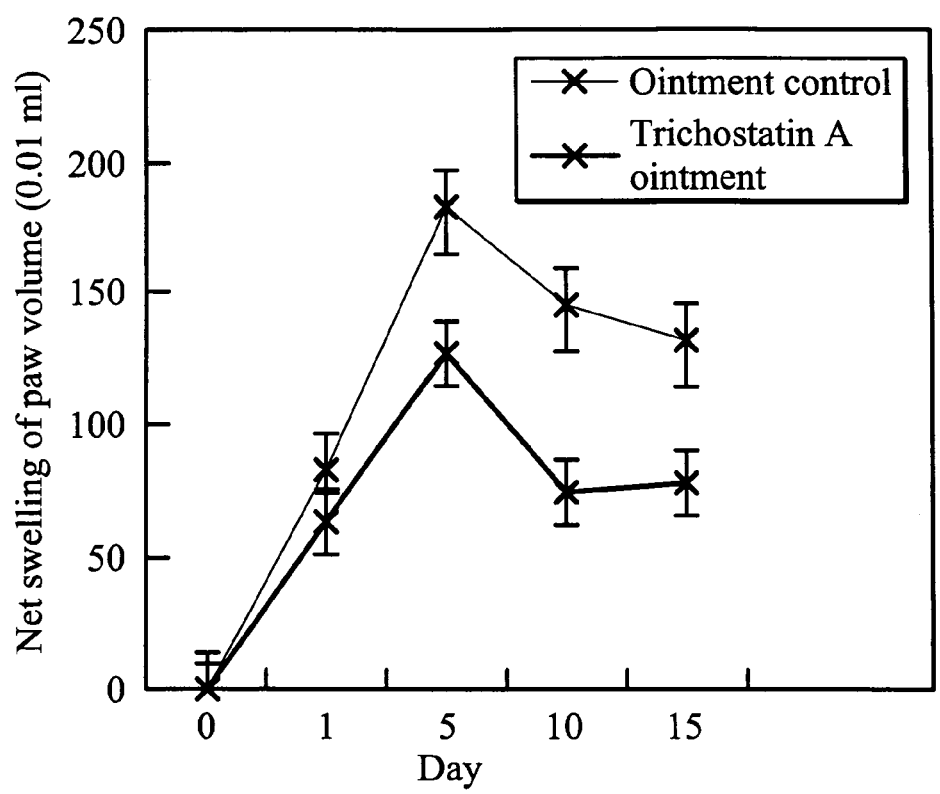

As shown in FIGS. 1A and 1B, the HDAC inhibitors suppress the ankle swelling more significantly when compared to the control groups, suggesting that there is an effect in anti-inflammation.

b. The HDAC inhibitor downregulates the proinflammatory cytokine TNF-α expression in the joint.

Figure 2:
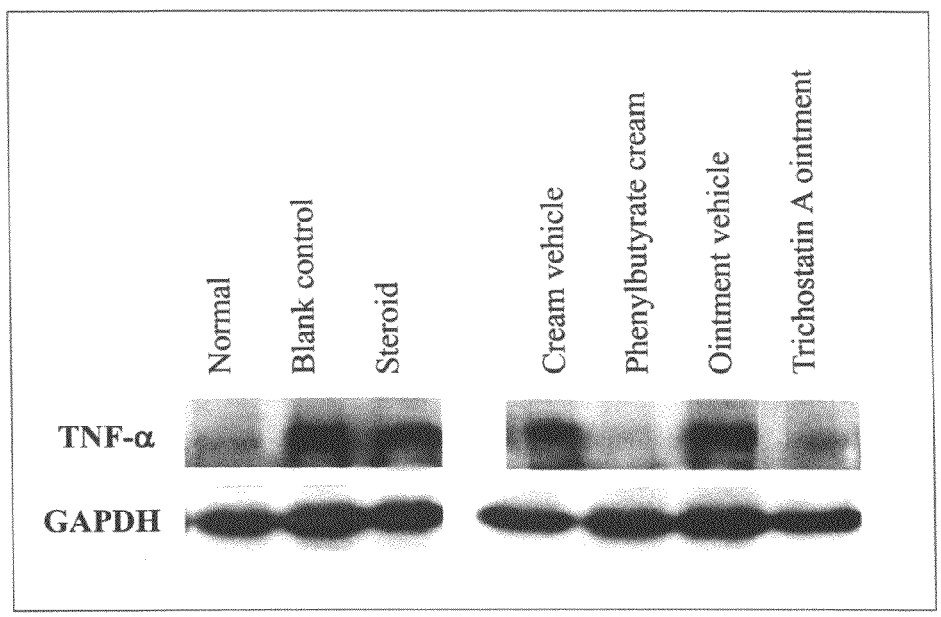
FIG. 2 is a northern blot result showing that the major proinflammatory cytokine TNF-$\alpha$ expression is significantly suppressed at the transcriptional level in the joint treated by the HDAC inhibitor.

As shown in FIG. 2, the northern blot shows that the HDAC inhibitors downregulate the TNF-α expression at the transcriptional level in the joint tissue, which is correlated with the anti-inflammation effect.

c. The HDAC inhibitor upregulates the cell cycle inhibitor in the cells lining the joint capsule.

Figure 3A:
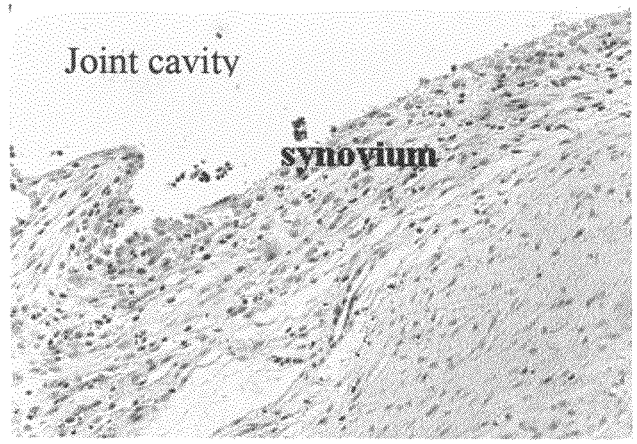
FIGS. 3A and 3B are histological staining results showing that the HDAC inhibitor upregulate the cell cycle inhibitor in the cells lining the joint capsule.
Figure 3B:

One representative example of immunohistochemistry of the cell cycle inhibitor, p16INK4, shown in FIG. 3B demonstrates that the HDAC inhibitors selectively upregulate p16INK4 expression in the synovium lining the joint capsule, suggesting that there is an effect in inhibition of synovial proliferation and invasion. FIG. 3A is a H&E staining of the joint cavity.

d. The HDAC inhibitors decrease degradation and resorption of cartilage and bone, preventing joint destruction.

Figure 4A:
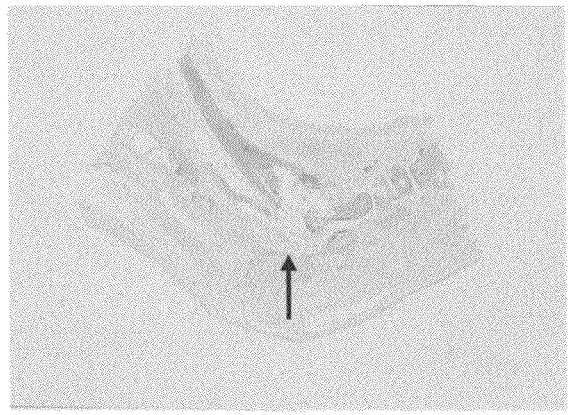
FIGS. 4A and 4B are the gross sections of the paw joints showing that the HDAC inhibitor preserves the joint structure.
Figure 4B:
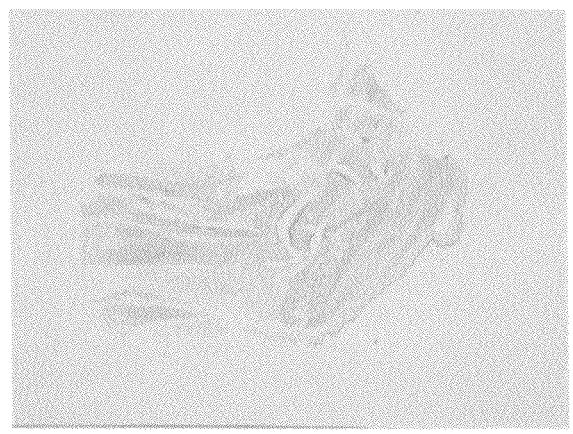
Figure 5A:
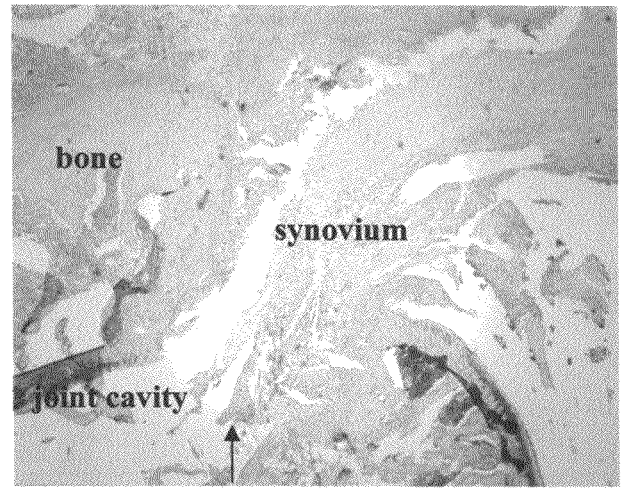
FIGS. 5A and 5B are histological staining results showing that the HDAC inhibitor prevents the joint destruction.
Figure 5B:
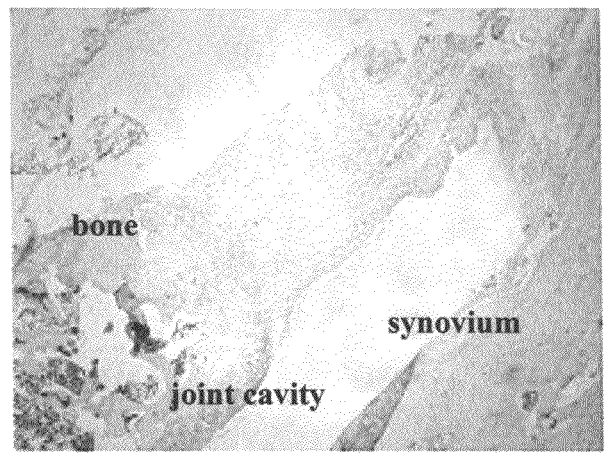
Figure 6A:
FIGS. 6A and 6B are histological straining results showing that the joint capsule is well protected by the HDAC inhibitor.
Figure 6B:
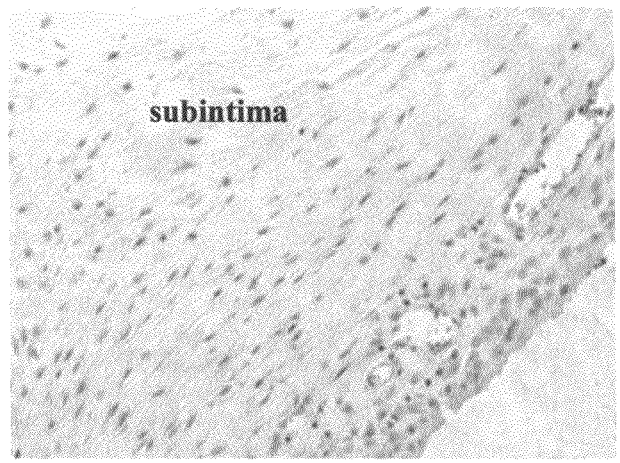

As shown in FIG. 4B, the gross section demonstrates that the whole joints in the right hind paw are well preserved in the groups treated with the HDAC inhibitors, compared to the blank control as shown in FIG. 4A. The pathological findings in FIGS. 5B and 6B further confirm that the HDAC inhibitors prevent the joint destruction from inflammatory cell infiltration, synovial invasion, cartilage degradation and bone resorption, respectively compared to the blank control as shown in FIGS. 5A and 6A.

Example 2

Prevention of Cartilage Resorption

Figure 7:
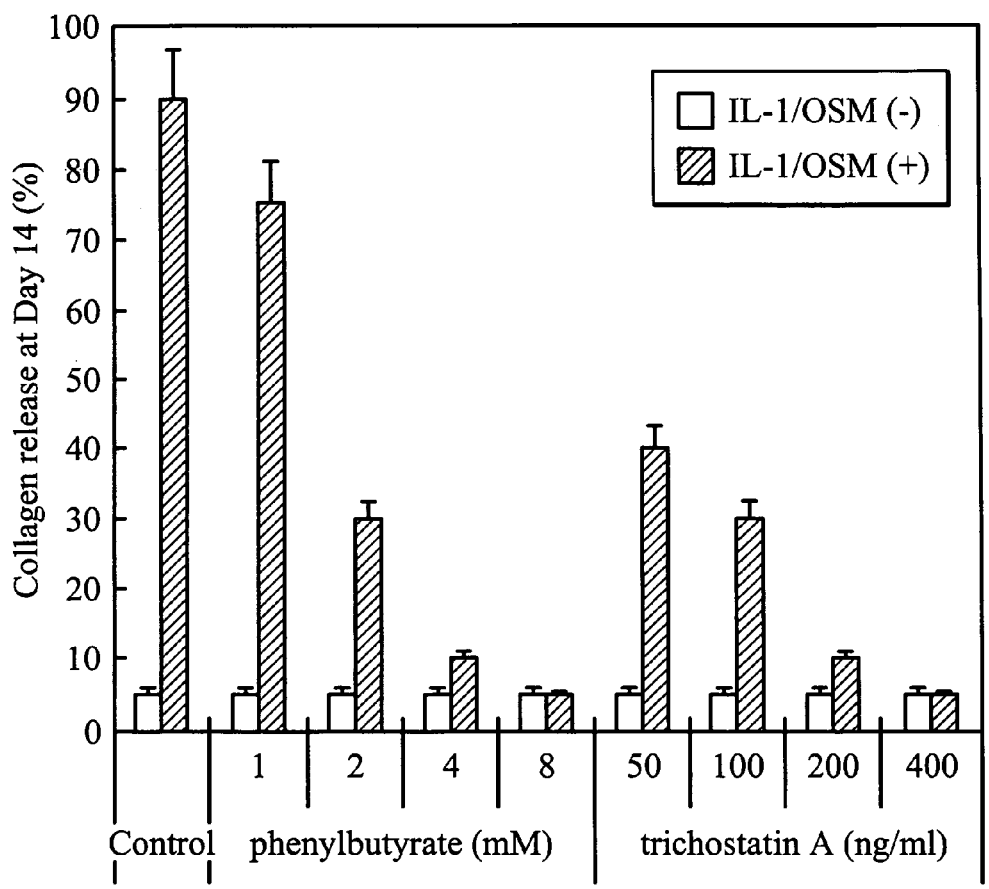
FIG. 7 is a diagram showing that the HDAC inhibitors, sodium phenylbutyrate and trichostatin A, decrease the IL-α and oncostatin M (OSM, an IL-6 type cytokine)-induced collagen release in a bovine nasal cartilage explant culture, suggesting that the HDAC inhibitors can prevent the cartilage resorption.

The combination of IL-1α and oncostatin M (OSM, an IL-6 type cytokine) has been shown to promote cartilage destruction (Cawston T E., et al., Arthritis Rheum. 41:1760-1771, 1998). A bovine nasal cartilage explant assay was performed to show the ability of the HDAC inhibitors in decreasing the cartilage resorption induced by IL-1α and OSM. The cartilage explant was cultured with IL-1α (5 ng/ml) and OSM (10 ng/ml), and treated with sodium phenylbutyrate (0-8 mM) or trichostatin A (0-400 ng.ml) for 12 hours. The percentage of collagen release from the cartilage explant into the conditioned culture medium represents the extent of cartilage resorption. As shown in FIG. 7, the HDAC inhibitors, sodium phenylbutyrate and trichostatin A, suppress the collagen loss from the cartilage. The result indicates the HDAC inhibitors can prevent the irreversible resorption of cartilage.

Other Embodiments

From the above description, one skilled in the art can easily ascertain the essential characteristics of the present invention, and without departing from the spirit and scope thereof, can make various changes and modifications of the invention to adapt it to various usages and conditions. For example, compounds structurally and functionally analogous to HDAC inhibitors described above can also be used to practice the present invention. Thus, other embodiments are also within the claims.

While the invention has been described by way of example and in terms of preferred embodiment, it is to be understood that the invention is not limited thereto.

What is claimed is:

1. A method for treating or reducing the risk of joint destruction in a joint or musculoskeletal disease, comprising
    identifying a subject suffering from the disease, and
    administering a composition consisting of a therapeutically effective amount of a histone deacetylase (HDAC) inhibitor or a pharmaceutically acceptable salt thereof and a pharmaceutically acceptable carrier to the subject,
    wherein the joint or musculoskeletal disease is selected from the group consisting of osteonecrosis, Paget's disease, Gaucher's disease, abnormally increased bone turnover, osteoclasis, periprosthetic osteolysis, degenerative joint disease, osteoarthritis, gouty arthritis, osteogenesis imperfecta, and a joint damage resulting from trauma, surgery, chemotherapy, or radiotherapy.

2. The method as claimed in claim 1, wherein the HDAC inhibitor is a hydroxamic acid-based hybrid polar compound, a short chain fatty acid (SCFA), a cyclic tetrapeptide, MS-27-275 [N-(2-aminophenyl)-4-[N(pyridin-3-yl-methoxycarbonyl)aminomethyl]benzamide], 3'-amino derivative of MS-27-275, CI-994, trifluoromethyl ketone, or an alpha-keto amide.

3. The method as claimed in claim 2, wherein the hydroxamic acid derivative is selected from the group consisting of suberoylanilide hydroxamic acid (SAHA), pyroxamide, M-carboxycinnamic acid bishydroxamide (CBHA), trichostatin A (TSA), trichostatin C, salicylihydroxamic acid (SBHA), azelaic bishydroxamic acid (ABHA), azelaic-1-hydroxamate-9-anilide (AAHA), 6-(3-chlorophenylureido) carpoic hydroxamic acid (3Cl-UCHA), oxamflatin, A-161906, scriptaid, PXD-101, LAQ-824, cyclic hydroxamic acid-containing peptide(CHAP), MW2796, and MW2996.

4. The method as claimed in claim 2, wherein the cyclic tetrapeptide is selected from the group consisting of trapoxin A, FR901228 (FK 228 or Depsipeptide), FR225497, apicidin, CHAP, HC-toxin, WF27082, and chlamydocin.

5. The method as claimed in claim 2, wherein the short chain fatty acid (SCFA) is selected from the group consisting of sodium butyrate, isovalerate, valerate, 4-phenylbutyrate (4-PBA), 4-phenylbutyrate sodium (PBS), arginine butyrate, propionate, butyramide, isobutyramide, phenylacetate, 3-bromopropionate, tributyrin, valproic acid, and valproate.

6. The method as claimed in claim 2, wherein the benzamide derivative is selected from the group consisting of CI-994, MS-27-275 (MS-275), and a 3'amino derivative of MS-27-275.

7. The method as claimed in claim 2, wherein the electrophilic ketone derivative is a trifluoromethyl ketone or an alpha-keto amide.

8. The method as claimed in claim 1, wherein the HDAC inhibitor is Depudecin.

9. The method as claimed in claim 1, wherein the administration is orally, intraarticularly, intraperitoneally, intrathecally, intrarterially, intranasally, intraparenchymally, subcutaneously, intramuscularly, intravenously, dermally, intrarectally, or topically.

10. The method as claimed in claim 1, wherein the histone deacetylase inhibitor or a pharmaceutically acceptable salt thereof and a pharmaceutical acceptable carrier are formulated as a cream, a gel, an ointment, a paste, a mouthwash, a powder, a tablet, a pill, a granule, a capsule, a lotion, a suspension, a liposome formulation, a nasosphere, a patch, a suppository, an enema, a drip infusion, or an injection solution.

11. A method for treating or reducing the risk of joint destruction in a joint or musculoskeletal disease, comprising
identifying a subject suffering from the disease, and
administering a composition consisting of a therapeutically effective amount of a histone deacetylase (HDAC) inhibitor or a pharmaceutically acceptable salt thereof and a pharmaceutically acceptable carrier to the subject.

12. The method of claim 1, wherein the joint or musculoskeletal disease is selected from the group consisting of osteonecrosis, Paget's disease, Gaucher's disease, abnormally increased bone turnover, osteoclasis, periprosthetic osteolysis, degenerative joint disease, gouty arthritis, osteogenesis imperfecta, and a joint damage resulting from trauma, surgery, chemotherapy, or radiotherapy.

13. The method of claim 1, wherein the joint or musculoskeletal disease is selected from the group consisting of Paget's disease, Gaucher's disease, degenerative joint disease, gouty arthritis, and a joint damage resulting from trauma, surgery, chemotherapy, or radiotherapy.

14. The method of claim 1, wherein the joint or musculoskeletal disease is osteoarthritis.

15. The method of claim 13, wherein the joint or musculoskeletal disease is selected from the group consisting of Gaucher's disease, degenerative joint disease, gouty arthritis, and a joint damage resulting from trauma, surgery, chemotherapy, or radiotherapy.

* * * * *